United States Patent
Lubkowitz et al.

(10) Patent No.: US 11,002,723 B2
(45) Date of Patent: May 11, 2021

(54) METHOD AND SYSTEM FOR CONTEMPORANEOUS ANALYSIS OF A CRUDE OIL FRONT END AND A CRUDE OIL BOILING POINT DISTRIBUTION VIA A SINGLE GAS CHROMATOGRAPH

(71) Applicant: SEPARATION SYSTEMS, INC., Gulf Breeze, FL (US)

(72) Inventors: Joaquin A. Lubkowitz, Gulf Breeze, FL (US); Claudio M. Ceccarelli, Gulf Breeze, FL (US); Roberto I. Meneghini, Gulf Breeze, FL (US)

(73) Assignee: SEPARATION SYSTEMS, INC., Gulf Breeze, FL (US)

( * ) Notice: Subject to any disclaimer, the term of this patent is extended or adjusted under 35 U.S.C. 154(b) by 108 days.

(21) Appl. No.: 15/989,867

(22) Filed: May 25, 2018

(65) Prior Publication Data
US 2018/0275113 A1    Sep. 27, 2018

Related U.S. Application Data

(63) Continuation-in-part of application No. 15/331,397, filed on Oct. 21, 2016, now Pat. No. 10,466,224.
(Continued)

(51) Int. Cl.
| | |
|---|---|
| *G01N 33/28* | (2006.01) |
| *G01N 30/46* | (2006.01) |
| *G01N 30/24* | (2006.01) |
| *G01N 30/02* | (2006.01) |
| *G01N 30/78* | (2006.01) |

(Continued)

(52) U.S. Cl.
CPC ........ *G01N 33/2823* (2013.01); *G01N 30/24* (2013.01); *G01N 30/466* (2013.01); *G01N 30/68* (2013.01); *G01N 30/78* (2013.01); *G01N 2030/025* (2013.01);
(Continued)

(58) Field of Classification Search
None
See application file for complete search history.

(56) References Cited

U.S. PATENT DOCUMENTS

| | | |
|---|---|---|
| 4,869,876 A | 9/1989 | Arfman et al. |
| 5,116,764 A | 5/1992 | Annino et al. |

(Continued)

FOREIGN PATENT DOCUMENTS

| | | |
|---|---|---|
| WO | WO 2010/101453 A2 | 9/2010 |
| WO | WO 2010/116389 A1 | 10/2010 |

OTHER PUBLICATIONS

M. Subramanian, M.D. Deo, F.V. Hanson, Compositional Analysis of Bitumen and Bitumen-Derived Products, Journal of Chromatographic Science, vol. 34, Issue 1, Jan. 1996, pp. 20-26, (Year: 1996).*

(Continued)

*Primary Examiner* — Paul M. West
*Assistant Examiner* — Mark A Shabman
(74) *Attorney, Agent, or Firm* — Arent Fox LLP

(57) ABSTRACT

A gas chromatography instrument comprising a first autoinjector in communication with a first column, a second autoinjector in communication with a second column, a first flame ionization detector in communication with the first column, a second flame ionization detector in communication with the second column, wherein the first column is housed in a first compartment and the second column is housed in a second compartment.

21 Claims, 2 Drawing Sheets

Related U.S. Application Data

(60) Provisional application No. 62/511,663, filed on May 26, 2017, provisional application No. 62/245,127, filed on Oct. 22, 2015.

(51) Int. Cl.
  *G01N 30/30* (2006.01)
  *G01N 30/68* (2006.01)
  *G01N 30/88* (2006.01)

(52) U.S. Cl.
  CPC ........... *G01N 2030/3007* (2013.01); *G01N 2030/3084* (2013.01); *G01N 2030/8854* (2013.01)

(56) References Cited

U.S. PATENT DOCUMENTS

| | | | | | |
|---|---|---|---|---|---|
| 5,699,269 | A | * | 12/1997 | Ashe | G01N 33/2823 702/30 |
| 6,530,260 | B1 | * | 3/2003 | Mustacich | G01N 30/30 210/198.2 |
| 6,711,532 | B1 | | 3/2004 | Spieksma | |
| 7,387,811 | B2 | * | 6/2008 | Selvamanickam | C23C 16/408 29/599 |
| 8,303,694 | B2 | * | 11/2012 | Tipler | G01N 30/7206 96/101 |
| 8,621,912 | B2 | | 1/2014 | Guieze | |
| 2007/0050154 | A1 | * | 3/2007 | Albahri | G01N 25/14 702/22 |
| 2008/0105032 | A1 | | 5/2008 | Reddy et al. | |
| 2013/0236276 | A1 | * | 9/2013 | Richter | B01L 3/00 414/222.07 |
| 2013/0276512 | A1 | * | 10/2013 | Bae | G01N 30/02 73/23.35 |
| 2014/0165841 | A1 | * | 6/2014 | Otsuka | G01N 30/6095 96/101 |

OTHER PUBLICATIONS

Extended Search Report communication from the European Patent Office in counterpart European Application No. 16858425.8, dated May 23, 2019.

International Search Report and Written Opinion of related International Patent Application No. PCT/US2016/058438 dated Jan. 3, 2017.

* cited by examiner

METHOD AND SYSTEM FOR CONTEMPORANEOUS ANALYSIS OF A CRUDE OIL FRONT END AND A CRUDE OIL BOILING POINT DISTRIBUTION VIA A SINGLE GAS CHROMATOGRAPH

CROSS-REFERENCE TO RELATED APPLICATIONS

This application is a continuation-in-part of U.S. patent application Ser. No. 15/331,397, entitled "Method and System for Contemporaneous Analysis of a Crude Oil Front End and a Crude Oil Boiling Point Distribution via a Single Gas Chromatograph," filed on Oct. 21, 2016, which claims priority from U.S. Provisional Patent Application No. 62/245,127, filed on Oct. 22, 2015. This application also claims priority from U.S. Provisional Patent Application No. 62/511,663, filed May 26, 2017. Each of the above-mentioned applications is expressly incorporated by reference herein in its entirety.

FIELD OF THE INVENTION

Aspect of the present invention relate in general to gas chromatography instruments, particularly for use in determining the composition of crude oils and fractions thereof.

BACKGROUND

Gas Chromatography is a means of chemical analysis used for separating chemicals in a complex sample. A gas chromatograph uses a narrow tube, known as a column, through which different chemical constituents of a sample pass in a gas stream. The gas stream is also called the carrier gas or mobile phase. Gas Liquid Chromatography (GLC), or simply Gas Chromatography (GC), is a type of chromatography in which the mobile phase is a gas. The mobile phase (i.e., a gas stream) is passed through a column with a phase coating, which is called the stationary phase and which is a microscopic layer of liquid on an inert solid wall of the column. The column is often flexible so that a very Jong column can be wound into a small coil. As the chemical constituents exit the end of the column, they are detected and identified electronically.

In GC, the chemical constituents within a sample pass through the column at different rates, depending on their various chemical and physical properties and their interaction with a specific column stationary phase. Chemical constituents are characterized by the different rates by which they flow through, or elute from, the column. This rate corresponds with the constituents' individual retention time (i.e., the length of time between the injection of the sample and the detection of the individual component). In many cases, constituents with different boiling points have different retention times. Other parameters can also be used to alter the order or retention time, such as the carrier gas flow rate and column temperature.

The column(s) in a GC are contained in an oven, the temperature of which is precisely controlled (e.g., electronically). The time it takes, a sample to pass through the column is directly proportional to the temperature of the column.

One application of GC is for the analysis of crude oil. Crude oil, for example, may contain a mixture of chemical compounds from a family of several hundred chemical compounds. Some chemicals that may be found in crude oil include n-paraffins (e.g., n-hexane), isoparaffins (e.g., isooctane), aromatics (e.g., benzene, toluene, xylenes), naphthene (e.g., cyclohexane), olefins (e.g., pentadiene). Crude oil also contains compounds of large molecular weight which are not capable to pass through GC columns. These compounds are called Asphaltenes.

One useful tool for analyzing crude oil is its boiling point (BP) curve, as boiling point range is often a key controlling parameter for manufacturing petroleum products, as well as pricing crude oil. GC is routinely employed for determining the boiling point range of oil products, as it is a fast and inexpensive method for providing information regarding the fuel-type present. A BP curve is a quantitative percent mass yield as a function of the boiling point of the hydrocarbon components of a sample.

However, in the case of crude oil, two column systems are often required since the crude oil BP curve obtained by high temperature columns is not accurate in the region of Initial Boiling Point up to 25% of the BP curve, generally comprising methane through n-dodecane. As a result, a second injection is conventionally made in a separate instrument to analyze the crude oil fraction in the region of methane through n-dodecane. This second injection is often analyzed and identified using a Detailed Hydrocarbon Analysis (DHA) column. The identification on this longer DHA column is often used for providing the boiling point in the region up to 25% of the crude components. In many cases, the DHA column requires different temperatures than the high temperature columns, thereby preventing both columns from being housed in a single gas chromatograph oven. Generally DHA columns are designed such that they have a limited temperature range and cannot coexist in the same oven as a crude oil column, which is heated to high temperatures. In addition, because of the DHA column's limited temperature range, it generally is not capable of receiving and/or analyzing an entire crude oil sample. Rather, the DHA column is generally only capable of receiving and analyzing portions of a sample in the region of methane through n-dodecane.

A presentation directed to various aspects of related art was given on Oct. 22, 2015, in Houston, Tex., a copy of which is attached hereto and is incorporated herein in its entirety.

SUMMARY AND DETAILED DESCRIPTION

Aspects of the present disclosure provide a gas chromatography instrument comprising: a first autoinjector in communication with a first column and a second autoinjector in communication with a second column, and a first flame ionization detector in communication with the first column and a second flame ionization detector in communication with the second column, wherein the first column is housed in a first compartment and the second column is housed in a second compartment.

Aspects of the present disclosure relate to Gas Chromatography (GC) systems and methods, which provide for more efficiently determining the composition of crude oils and fractions thereof. Systems and methods in accordance with aspects of the present disclosure advantageously avoid the use of two separate instruments, which have previously been required due to different operational temperatures of the columns utilized in GC crude oil analysis, for example. Systems and methods in accordance with aspects of the present disclosure allow the characterization of a crude oil in one single instrument by the contemporaneous injection of a crude oil sample into two columns, thereby saving both time and expense. In addition the system provides an accurate boiling point curve of the entire crude oil sample.

Figure 1:
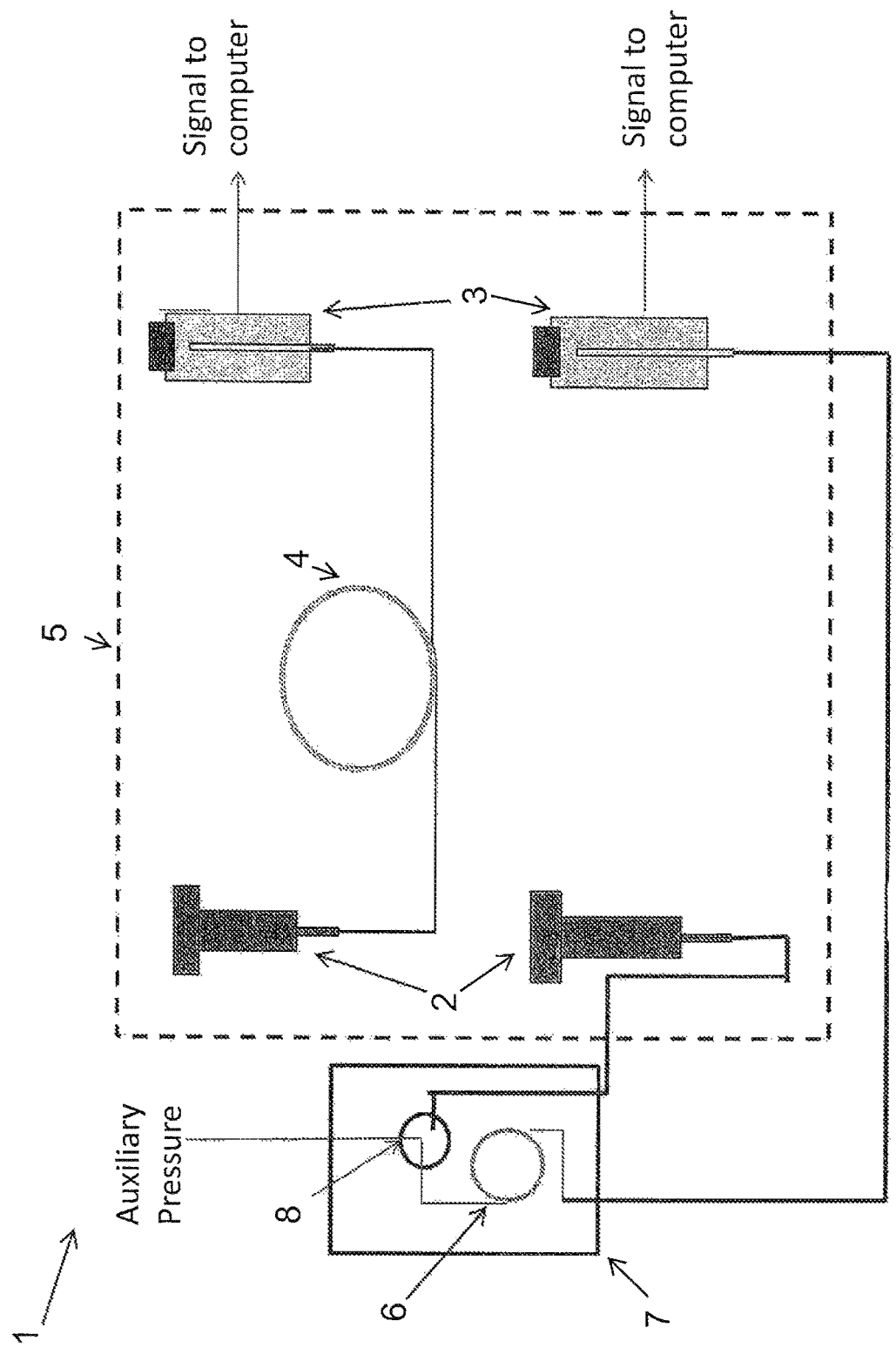
FIG. 1 shows an example of a GC system in accordance with aspects of the present disclosure.

An example of a GC system according to aspects of the present disclosure is shown in FIG. 1. According to aspects of the present disclosure, the system may comprise a single GC instrument (1), wherein the instrument includes two autoinjectors (2), a first column and a second column, one temperature programmable inlet, a split splitless inlet, and two flame ionization detectors (3).

According to some variations, aspects of the present disclosure may include a GC instrument comprising or consisting of two capillary columns, each column being housed in a separate space or compartment in the GC instrument. For example, as shown in FIG. 1, a first capillary column (4) may be housed in a main GC oven (5), while a second capillary column (6) may be housed in a separate compartment (7) other than the main GC oven.

According to some aspects, the first capillary column (4) and the second capillary column (6) may be different. For example, the first capillary column (4) may be or comprise a metal column, while the second capillary column (6) may be or comprise a DHA column. Alternatively or additionally, the first capillary column (4) and the second capillary column (6) may be configured to perform different test methods. For example, the first capillary column (4) may be configured to perform ASTM D7169 (Standard Test Method for Boiling Point Distribution of Samples with Residues Such as Crude Oils and Atmospheric and Vacuum Residues by High Temperature Gas Chromatography) while the second capillary column (6) may be configured to perform ASTM D7900 (Standard Test Method for Determination of Light Hydrocarbons in Stabilized Crude Oils by Gas Chromatography). According to some aspects, the first capillary column (4) and the second capillary column (6) may be configured such the data provided by each column may together, for example, provide a complete and accurate BP curve for a crude oil sample, and/or a more complete result than systems of the related art.

According to some aspects, the first capillary column (4) and the second capillary column (6) may have different sample requirements. For example, each column may require a sample to be diluted with a solvent prior to injection into the column. According to some aspects, the first capillary column (4) may require a sample to be diluted to 2% with an appropriate solvent, while the second capillary column (6) may require a sample to be diluted to 5% with an appropriate solvent. Examples of appropriate solvents according to the present disclosure include, but are not limited to, carbon disulfide, methylene chloride, and chloroform. According to some aspects, the second capillary column may require an internal standard. As used herein, the term "internal standard" refers to a chemical substance that is added in a constant amount to a sample. In the case of the second capillary column, the internal standard may comprise a known substance that does not exist in crude oil and allows correction of DHA data for the portion of the crude oil that does not enter into the DHA column.

According to aspects of the present disclosure, the separate compartment (7) may be configured to thermally house the second column (6), e.g., a DHA column. For example, the separate compartment may be an insulated thermal housing which is configured to isolate the second column (6), e.g., a DHA column, from other compartments of the GC instrument and/or the environment.

According to aspects of the present disclosure, the second column (6), e.g., a DHA column, may be heated. For example, the DHA column may be heated by electronics in the GC instrument, such as electronics that are already present in the GC instrument to control heat for the first column, thereby not requiring specific and/or additional heating electronics. That is, an electronic device that provides heat to the second column may also provide heat to at least one other component of the instrument. In some embodiments, the DHA column may be encased by or wrapped with a thin film heater. According to aspects of the present disclosure, the DHA column may be uniformly heated with a heater. For example, the heater may comprise a wire in a thin film. According to some aspects, the heater may be configured to be compatible with the wattage produced by electronics in the GC instrument. The heater, such as the thin film heater, may, for example, be covered with aluminum foil or other similarly performing material.

According to some aspects of the present disclosure, the heated DHA column surprisingly provides repeatable retention times through analysis times up to about 30-45 minutes.

According to aspects of the present disclosure, the instruments may be provided with features for controlling and/or limiting the temperature of one or both capillary columns, wherein the features may comprise, for example, a controller. For example, the temperature of the DHA column may be controlled by the controller and/or other features so as to not rise above about 300° C. (i.e., to a maximum of about 300° C.). In some embodiments, the DHA column may be temperature sensitive. According to some aspects, the temperature of the first capillary column may be controlled so as to reach a temperature necessary for the boiling point determination of a sample, such as a crude oil sample. For example, the temperature of the first capillary column may be controlled so as to reach a temperature of at least 430° C.

According to aspects of the present disclosure, as shown in FIG. 1, the compartment (7) that houses the second column (6), e.g., a DHA column, may comprise a cooling mechanism, for example a solenoid activated cooling valve and/or a liquid coolant distributor. The liquid coolant distributor may comprise a liquid coolant valve and a shower head configured to distribute coolant uniformly. Examples of coolants useful according to aspects of the present disclosure include, but are not limited to, liquid carbon dioxide and liquid nitrogen. In some embodiments, the shower head may comprise a circular shower head portion. According to some aspects, the shower head may be configured such that a liquid, e.g., liquid coolant, distributed therethrough is distributed through two or more orifices. According to some aspects, the shower head is configured such that a liquid, e.g., liquid coolant, is distributed through multiple orifices in the shower head. The liquid coolant valve and the shower head together may be configured to allow rapid cooling at the end of a heating cycle and/or operation at sub-ambient temperatures, for example. As used herein, the term "sub-ambient" refers to a temperature below ambient temperature, wherein in some embodiments ambient temperature may be from about 20 to 25° C.

According to aspects of the present disclosure, the compartment that houses the DHA column may also house a microfluidic switch (8). In some embodiments, the microfluidic switch (8) may be configured to allow a preselected fraction of a sample to enter the DHA column. For example, the preselected fraction may comprise part or all of the portion of the sample that is within the region of methane through nonane and/or that comprises components having one or more boiling points of below about 300° C. According to some aspects, the microfluidic switch (8) may prevent any portion of the sample comprising components having a higher boiling point that n-nonane or having a higher boiling point than about 300° C. from entering the DHA column. According to some embodiments, the microfluidic switch may also be heated. The microfluidic switch (8) may be, for example, heated independently from either capillary column.

According to some aspects of the present disclosure, the instrument may be provided with one or more backflush devices configured to provide a reverse flow of fluid (including liquids and/or other components, including gases and vapors, interchangeably referred to herein as "fluid") through one or both capillary columns. As used herein, "reverse flow" refers to a flow of such fluid through a capillary column in a direction opposite to the direction of flow of a sample through the column. According to some aspects, the instrument may comprise a first backflush device which is configured to provide a reverse flow through the first capillary column after a predetermined amount of time. For example, the predetermined amount of time may be the amount of time necessary for one or more samples to elute from the first column. In this way, at least some of the damaging components left behind by the one or more samples may be substantially or completely removed from the column, thereby preserving the integrity of the column. The instrument may additionally or alternatively comprise a second backflush device which is configured to provide a reverse fluid flow through the second capillary column after a predetermined amount of time, for example, the amount of time necessary for one or more samples to elute from the second column.

According to aspects of the present disclosure, the system may also be configured to utilize one or more separate computer systems. For example, certain embodiments include two separate computer systems (i.e., a first computer system and a second computer system) wherein the first computer system may be used to provide the boiling point curve of a crude oil sample obtained in a first capillary column (4), and the second computer system may be used to identify components, such as those from methane through nonane, obtained in the second column (6). For example, the first capillary column and first computer system may provide data for components in a fluid having a boiling point above about 300° C., while the second capillary column and second computer system may provide data for components having a boiling point at or below about 300° C. It should be understood that this temperature (i.e., the specific temperature at which the two curves are defined) may be selected by a user, depending on the situation (e.g., 170° C. instead of 300° C.).

In some embodiments, the instrument may comprise another separate computer system (e.g., a third computer system) capable of merging the two BP curves, thereby rendering a final, accurate BP curve. For example, the final BP curve may include data corresponding to all components of a sample, that is, both those components having a boiling point above about 300° C. (or any other selected temperature) and those components having a boiling point at or below about 300° C. (or any other selected temperature). In some embodiments, the computer system capable of merging the two BP curves may be comprised within the same system used to identify components (i.e., the second computer system), such as those from methane through nonane, obtained in the DHA column.

Figure 2:
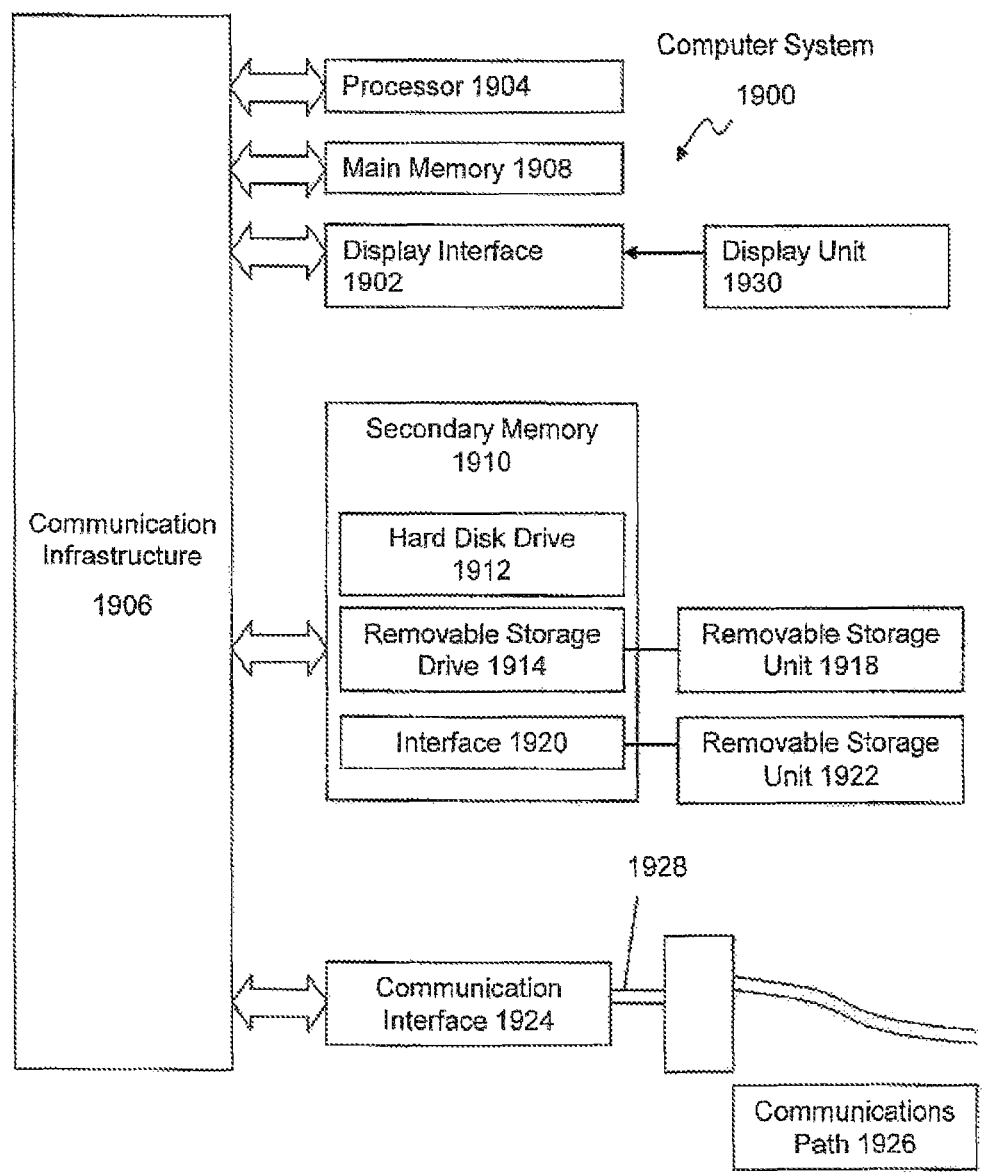
FIG. 2 shows an example computer system for use in accordance with aspects of the present disclosure.

Aspects of the present disclosure may be implemented using hardware, software or a combination thereof and may be implemented in one or more computer systems or other processing systems. In one variation, aspects of the present disclosure are directed toward one or more computer systems capable of carrying out the functionality described herein. An example of such a computer system 1900 is shown in FIG. 2.

Computer system 1900 includes one or more processors, such as processor 1904. The processor 1904 is connected to a communication infrastructure 1906 (e.g., a communications bus, cross-over bar, or network). Various software aspects are described in terms of this exemplary computer system. After reading this description, it will become apparent to a person skilled in the relevant art(s) how to implement the aspects of present disclosure using other computer systems and/or architectures.

Computer system 1900 can include a display interface 1902 that forwards graphics, text, and other data from the communication infrastructure 1906 (or from a frame buffer not shown) for display on the display unit 1930. Computer system 1900 also includes a main memory 1908, preferably random access memory (RAM), and may also include, a secondary memory 1910. The secondary memory 1910 may include, for example, a hard disk drive 1912 and/or, a removable storage drive 1914, representing a floppy disk drive, a magnetic tape drive, an optical disk drive, etc. The removable storage drive 1914 reads from and/or writes to a removable storage unit 1918 in a well-known manner. Removable storage unit 1918, represents a floppy disk, magnetic tape, optical disk, etc., which is read by and written to removable storage drive 1914. As will be appreciated, the removable storage unit 2018 includes a computer usable storage medium having stored therein computer software and/or data.

In alternative variations, secondary memory 1910 may include other similar devices for allowing computer programs or other instructions to be loaded into computer system 1900. Such devices may include, for example, a removable storage unit 1922 and an interface 2920. Examples of such may include a program cartridge and cartridge interface (such as that found in video game devices), a removable memory chip (such as an erasable programmable read only memory (EPROM), or programmable read only memory (PROM)) and associated socket, and other removable storage units 1922 and interfaces 1920, which allow software and data to be transferred from the removable storage unit 1922 to computer system 1900.

Computer system 1900 may also include a communications interface 1924. Communications interface 1924 allows software and data to be transferred between computer system 1900 and external devices. Examples of communications interface 1924 may include a modem, a network interface (such as an Ethernet card), a communications port, a Personal Computer Memory Card International Association (PCMCIA) slot and card, etc. Software and data transferred via communications interface 1924 are in the form of signals 1928, which may be electronic, electromagnetic, optical or other signals capable of being received by communications interface 1924. These signals 1928 are provided to communications interface 1924 via a communications path (e.g., channel) 1926. This path 1926 carries, signals 1928 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 1914, a hard disk installed in hard disk drive 1912, and signals 1928. These computer program products provide software to the computer system 1900. Aspects of the present disclosure are directed to such computer program products.

Computer programs (also referred to as computer control logic) are stored in main memory 1908 and/or secondary memory 1910. Computer programs may also be received via communications interface 2024. Such computer programs, when executed, enable the computer system 1900 to perform the features in accordance with aspects of the present disclosure, as discussed herein. In particular, the computer programs, when executed, enable the processor 1904 to perform such features. Accordingly, such computer programs represent controllers of the computer system 1900.

In a variation where aspects of the present disclosure are implemented using software, the software may be stored in a computer program product and loaded into computer system 1900 using removable storage drive 1914, hard drive 1912, or communications interface 1924. The control logic (software), when executed by the processor 1904, causes the processor 1904 to perform the functions as described herein. In another variation, aspects of the present disclosure are implemented primarily in hardware using, for example, hardware components, such as application specific integrated circuits (ASICs). Implementation of the hardware state machine so as to perform the functions described herein will be apparent to persons skilled in the relevant art(s).

In yet another variation, aspects of the present disclosure are implemented using a combination of both hardware and software.

While aspects of this present disclosure have been described in conjunction with the example features outlined above, alternatives, modifications, variations, improvements, and/or substantial equivalents, whether known or that are or may be presently unforeseen, may become apparent to those having ordinary skill in the art. Accordingly, the example aspects of the present disclosure, as set forth above, are intended to be illustrative, not limiting. Various changes may be made without departing from the spirit thereof. Therefore, aspects of the present disclosure are intended to embrace all known or later-developed alternatives, modifications, variations, improvements, and/or substantial equivalents.

What is claimed is:

1. A gas chromatography instrument, comprising:
    a first autoinjector in communication with a first column and a second autoinjector in communication with a second column, and
    a first flame ionization detector in communication with the first column and a second flame ionization detector in communication with the second column,
    wherein the first column is housed in a first compartment and the second column is housed in a second compartment,
    wherein the first column contains features for and is configured to perform ASTM D7169 method for determining boiling point distribution of samples comprising crude oils and atmospheric and vacuum residues, and the second column contains features for and is configured to perform ASTM D7900 method for determining light hydrocarbons present in stabilized crude oil, and
    wherein results of the test methods performed in the first and the second column, when combined, provide a more complete boiling point distribution of a crude oil sample than that provided by the result of the method performed in the first or the second column alone.

2. The gas chromatography instrument of claim 1, wherein the first compartment comprises an oven.

3. The gas chromatography instrument of claim 1, wherein the second compartment comprises an insulated thermal housing.

4. The gas chromatography instrument of claim 1, wherein the second column is a Detailed Hydrocarbon Analysis (DHA) column.

5. The gas chromatography instrument of claim 1, further comprising a heater configured to heat the second column.

6. The gas chromatography instrument of claim 5, wherein the heater is a thin film heater.

7. The gas chromatography instrument of claim 5, wherein the heater heats the second column to a maximum of 300° C.

8. The gas chromatography instrument of claim 1, wherein an electronic device that provides heat to the second column also provides heat to at least one other component of the instrument.

9. The gas chromatography instrument of claim 1, further comprising a first controller that controls the temperature of the first column.

10. The gas chromatography instrument of claim 9, wherein the first controller is configured such that the temperature of the first column is at least a temperature necessary to determine a boiling point of a sample being analyzed in the first column.

11. The gas chromatography instrument of claim 9, further comprising a backflush device.

12. The gas chromatography instrument of claim 1, wherein the second compartment comprises a liquid coolant distributor.

13. The gas chromatography instrument of claim 1, wherein the second compartment comprises a microfluidic switch.

14. The gas chromatography instrument of claim 13, wherein the microfluidic switch is configured to provide a preselected fraction of a sample to the second column.

15. The gas chromatography instrument of claim 14, wherein the preselected fraction comprises a portion of the sample having components with a boiling points of below about 300° C.

16. The gas chromatography instrument of claim 1, further comprises a first computer system and a second computer system.

17. The gas chromatography instrument of claim 16, wherein the first computer system utilizes data obtained from the first column to provide a boiling point curve of a sample being analyzed in the first column.

18. The gas chromatography instrument of claim 16, wherein the second computer system utilizes data obtained from the second column to identify a component of a sample being analyzing in the second column.

19. The gas chromatography instrument of claim 16, further comprising a third computer system, wherein the third computer system utilizes data from both the first computer system and the second computer system to provide a final BP curve.

20. The gas chromatography instrument of claim 1, wherein the first column is configured to be heated to at least 430° C.

21. The gas chromatography instrument of claim 1, wherein the first column is a metal column.

\* \* \* \* \*